United States Patent
Faries, Jr. et al.

(10) Patent No.: US 6,384,380 B1
(45) Date of Patent: May 7, 2002

(54) TEMPERATURE CONTROLLED CABINET SYSTEM AND METHOD FOR HEATING ITEMS TO DESIRED TEMPERATURES

(75) Inventors: Durward I. Faries, Jr., McLean; Bruce R. Heymann, Vienna; Calvin Blankenship, Centreville, all of VA (US)

(73) Assignee: Medical Solutions, Inc., Chantilly, VA (US)

( * ) Notice: Subject to any disclaimer, the term of this patent is extended or adjusted under 35 U.S.C. 154(b) by 0 days.

(21) Appl. No.: 09/684,863

(22) Filed: Oct. 6, 2000

Related U.S. Application Data (60) Provisional application No. 60/158,507, filed on Oct. 8, 1999.

(51) Int. Cl.[7] .............................. A61F 7/00; F27D 11/02; F27D 19/00
(52) U.S. Cl. ...................... 219/385; 219/394; 219/395; 219/399; 219/428; 604/114
(58) Field of Search .................................. 219/385, 394, 219/395, 405, 399, 428; 222/146.5; 312/236; 6604/114, 291

(56) References Cited

U.S. PATENT DOCUMENTS

| | | | |
|---|---|---|---|
| 1,659,719 A | | 1/1928 | Blake |
| 2,214,215 A | | 9/1940 | Watermann et al. |
| 2,576,874 A | | 11/1951 | Acton |
| 2,713,112 A | | 7/1955 | Mills et al. |
| 2,741,099 A | | 4/1956 | Beane |
| 2,841,132 A | | 7/1958 | Philipp |
| 2,885,526 A | * | 5/1959 | Paulding ..................... 219/394 |
| 2,994,760 A | | 8/1961 | Pecoraro et al. |
| 3,051,582 A | * | 8/1962 | Muckler et al. ............ 219/386 |
| 3,193,339 A | * | 7/1965 | Cooper ....................... 312/123 |
| 3,241,603 A | | 3/1966 | Nagata |
| 3,255,812 A | | 6/1966 | Bayane et al. |

(List continued on next page.)

FOREIGN PATENT DOCUMENTS

| | | |
|---|---|---|
| DE | 37 42 927 | 7/1989 |
| DE | 197 52 578 | 6/1999 |
| WO | WO 98/45658 | 10/1998 |

OTHER PUBLICATIONS

Cahill, New Name, New Helmsman, JEMS, Aug. 1996.
CBi Healthcare Systems, Inc., Controlled Temperature Cabinet System, JEMS, Mar. 1997.
Koolatron, P–34 PC–3 Precision Control Thermoelectric Cooler/Warmer, Jan. 1998.

(List continued on next page.)

Primary Examiner—Joseph Pelham

(57) ABSTRACT

A temperature control system includes a cabinet or system housing having a plurality of heating compartments for containing intravenous solution bags or other medical items. Each heating compartment is independently heat controlled via a controller, and includes a heating assembly including a heater, a U-shaped heating plate, a temperature sensor and a cut-out switch for disabling the heater when a threshold temperature is exceeded. The desired or set point temperature for each heating compartment may be independently entered to the controller via an input device. The heating plate has a generally U-shaped configuration with a thermally conductive bottom wall and thermally conductive side walls extending therefrom. The heater is typically affixed to the underside of the bottom wall, wherein, upon heating of the bottom wall, heat is conducted through the side walls to provide an even distribution of heat to medical items placed within the heating compartment. Each heating compartment may further include a collapsible rack structure allowing a user to selectively partition each heating compartment based upon the specific types of medical items to be heated.

43 Claims, 5 Drawing Sheets

U.S. PATENT DOCUMENTS

| | | | | |
|---|---|---|---|---|
| 3,329,202 | A | 7/1967 | Birman | |
| 3,353,589 | A | 11/1967 | Tope et al. | |
| 3,386,498 | A | 6/1968 | Funfstuck | |
| 3,485,245 | A | 12/1969 | Lahr et al. | |
| 3,536,132 | A | 10/1970 | Pecoraro et al. | |
| 3,590,215 | A | 6/1971 | Anderson et al. | |
| 3,612,165 | A | 10/1971 | Haynes | |
| 3,713,302 | A | 1/1973 | Reviel | |
| 3,777,187 | A | 12/1973 | Kohn | |
| 3,826,305 | A | 7/1974 | Fishman | |
| 3,858,106 | A | 12/1974 | Launius | |
| 3,879,171 | A | * 4/1975 | Tulis | 219/521 |
| 4,024,377 | A | 5/1977 | Henke | |
| 4,084,080 | A | 4/1978 | McMahan | |
| 4,189,995 | A | 2/1980 | Löhr et al. | |
| 4,233,495 | A | 11/1980 | Scoville et al. | |
| 4,309,592 | A | 1/1982 | Le Boeuf | |
| 4,318,276 | A | 3/1982 | Sato et al. | |
| 4,328,676 | A | 5/1982 | Reed | |
| 4,331,859 | A | 5/1982 | Thomas et al. | |
| 4,364,234 | A | 12/1982 | Reed | |
| 4,407,133 | A | 10/1983 | Edmonson | |
| 4,419,568 | A | * 12/1983 | Overloop | 219/386 |
| 4,455,478 | A | 6/1984 | Guibert | |
| 4,464,563 | A | 8/1984 | Jewett | |
| 4,495,402 | A | 1/1985 | Burdick et al. | |
| 4,523,078 | A | 6/1985 | Lehmann | |
| 4,605,840 | A | 8/1986 | Koopman | |
| 4,657,004 | A | 4/1987 | Coffey | |
| 4,678,460 | A | 7/1987 | Rosner | |
| 4,707,587 | A | 11/1987 | Greenblatt | |
| 4,726,193 | A | 2/1988 | Burke et al. | |
| 4,745,248 | A | 5/1988 | Hayes | |
| 4,801,777 | A | 1/1989 | Auerbach | |
| 4,823,554 | A | 4/1989 | Trachtenberg et al. | |
| 4,874,033 | A | 10/1989 | Chatelain et al. | |
| 4,894,207 | A | 1/1990 | Archer et al. | |
| 4,906,816 | A | 3/1990 | van Leerdam | |
| 4,910,386 | A | 3/1990 | Johnson | |
| 4,935,604 | A | 6/1990 | Allen et al. | |
| 4,961,320 | A | 10/1990 | Gutmann | |
| 5,061,241 | A | 10/1991 | Stephens, Jr. et al. | |
| 5,061,630 | A | 10/1991 | Knopf et al. | |
| 5,081,697 | A | 1/1992 | Manella | |
| 5,106,373 | A | 4/1992 | Augustine et al. | |
| 5,108,372 | A | 4/1992 | Swenson | |
| 5,183,994 | A | 2/1993 | Bowles, Sr. et al. | |
| 5,195,976 | A | 3/1993 | Swenson | |
| 5,217,064 | A | 6/1993 | Kellow et al. | |
| 5,243,833 | A | 9/1993 | Coelho et al. | |
| 5,263,929 | A | 11/1993 | Falcone et al. | |
| 5,276,310 | A | 1/1994 | Schmidt et al. | |
| 5,282,264 | A | 1/1994 | Reeves et al. | |
| 5,297,234 | A | 3/1994 | Harms et al. | |
| 5,315,830 | A | 5/1994 | Doke et al. | |
| 5,333,326 | A | 8/1994 | Faries, Jr. et al. | |
| 5,345,923 | A | 9/1994 | Luebke et al. | |
| 5,364,385 | A | 11/1994 | Harms et al. | |
| 5,381,510 | A | 1/1995 | Ford et al. | |
| 5,397,875 | A | 3/1995 | Bechtold, Jr. | |
| 5,399,007 | A | 3/1995 | Marconet | |
| 5,408,576 | A | 4/1995 | Bishop | |
| 5,483,799 | A | 1/1996 | Dalto | |
| 5,572,873 | A | 11/1996 | Lavigne et al. | |
| 5,653,905 | A | * 8/1997 | McKinney | 219/399 |
| 5,661,978 | A | 9/1997 | Holmes et al. | |
| 5,729,653 | A | 3/1998 | Magliochetti et al. | |
| 5,733,263 | A | 3/1998 | Wheatman | |
| 5,786,568 | A | 7/1998 | McKinney | |
| 5,879,329 | A | 3/1999 | Ginsburg | |
| 5,910,210 | A | 6/1999 | Violi et al. | |
| 5,924,289 | A | 7/1999 | Bishop, II | |
| 5,977,520 | A | * 11/1999 | Madson, Jr. et al. | 219/429 |
| 5,986,239 | A | * 11/1999 | Corrigan, III et al. | 219/385 |
| 5,989,238 | A | 11/1999 | Ginsburg | |
| 6,124,572 | A | 9/2000 | Spilger et al. | |
| 6,175,099 | B1 | * 1/2001 | Shei et al. | 219/394 |

OTHER PUBLICATIONS

Koolatron, Canadian company announces the release of a precision control unit, Aug. 1997.

ANTON, 500 miles from nowhere, it'll give you a cold drink or a warm burger . . ., Technology Update, 1993.

Koolatron, 1997 U.S. $ Price List, 1997.

Kellow et al. Drug Adulteration In Prehospital Emergency Medical Services, Oct. 1994.

CBi Medical, Inc., IV Fluid Warmer Model 8362, 1992.

Faries, Jr. et al., U.S. patent application Ser. No. 09/413,532, filed Oct. 6, 1999.

Faries, Jr. et al., U.S. patent application Ser. No. 09/419,664, filed Oct. 15, 1999.

* cited by examiner

TEMPERATURE CONTROLLED CABINET SYSTEM AND METHOD FOR HEATING ITEMS TO DESIRED TEMPERATURES

CROSS-REFERENCE TO RELATED APPLICATIONS

This application claims priority from U.S. Provisional Patent Application Serial No. 60/158,507, entitled "Temperature Controlled Cabinet System and Method for Heating Items to Desired Temperatures", and filed Oct. 8, 1999. The disclosure of the above-mentioned provisional application is incorporated herein by reference in its entirety.

BACKGROUND OF THE INVENTION

1. Technical Field

The present invention pertains to systems for heating medical items. In particular, the present invention pertains to a system for heating and maintaining medical solution containers (e.g., bags or bottles containing saline or intravenous (IV) solutions, antibiotics or other drugs, blood, etc.) or other medical items (e.g., instruments, blankets, etc.) at desired temperatures by providing an even distribution of heat to the medical items placed within the system.

2. Discussion of Related Art

Generally, various items are required to be heated prior to utilization in a medical procedure to prevent thermal shock and injury to a patient. These items typically include intravenous solution, surgical instruments, bottles and blankets. In order to provide the necessary heated items for use in medical procedures, medical personnel may utilize several types of warming systems to heat items toward their operational temperatures. For example, ovens may be disposed within operating rooms to heat items to desired temperatures. Further, U.S. Pat. No. 4,419,568 (Van Overloop) discloses a wet dressings heater having a base with side walls defining a cavity, and an insert connected to the base and defining at least one recess in the cavity for receiving wet dressings. A heater has an electrical heating element in close proximity to the insert recess for heating the wet dressings, while the temperature of the heating element is controlled in a desired temperature range for those wet dressings.

U.S. Pat. No. 4,495,402 (Burdick et al) discloses a warmer for heating wet dressings and other articles disposed within a heating and storage compartment. The articles are arranged within the compartment in stacked relation and disposed on a plate that is supplied with thermal energy from a heater. The plate includes a center aperture whereby a first thermal sensor is disposed in the aperture in contact with a bottommost article. Control circuitry is disposed beneath the plate to control the heater to maintain temperature of the bottommost article at a desired level based on the temperatures sensed by the first thermal sensor and a second thermal sensor responsive to heater temperature.

U.S. Pat. No. 5,408,576 (Bishop) discloses an intravenous fluid warmer having a cabinet structure to accommodate a plurality of intravenous fluid bags. A temperature sensor and pad of heating filaments are disposed within the cabinet structure, whereby the temperature sensor enables automatic temperature regulation of the pad of heating filaments to heat the intravenous fluid bags. The heating filaments are covered by a rubber layer to prevent melting of the bags during heating. A temperature indicator disposed on the cabinet structure permits a user to ascertain when a desired temperature is attained, whereby an intravenous fluid bag is removed from the intravenous fluid warmer via an opening defined in a side of the cabinet structure.

U.S. Pat. No. 5,986,239 (Corrigan, III et al.) discloses a conductive warmer for flexible plastic bags. The warmer includes a heat-conducting member of thermally conductive material having a plurality of fins which are parallel and spaced apart to define a plurality of bag-receiving compartments. The fins are connected to a back portion of the heat-conducting member to which a heating element is attached in a heat-exchanging relationship. The heating element conducts heat through the back portion and fins of the heat-conducting member to the bags.

In addition, the related art provides warming systems for other types of items. For example, U.S. Pat. No. 4,605,840 (Koopman) discloses a horizontal holding cabinet for prepared food, wherein the cabinet has a plurality of drawer-containing modules arranged side-by-side to each other. Each module has a heating element and an integral water reservoir and is capable of being independently heated and humidified. The modules each further include a drawer receiving cavity having an open front adapted to receive a drawer frame. The cavity bottom wall is provided with one or more heating elements, whereby the module walls conduct heat to heat the cavity. A temperature thermostat is mounted on the undersurface of the cavity bottom wall to sense cavity temperature and is further connected to a thermostatic controller that controls the heating elements in accordance with a desired temperature.

The warming systems described above suffer from several disadvantages. In particular, ovens typically do not have a high degree of accuracy or control, thereby enabling use of items having temperatures incompatible with a medical procedure and possibly causing injury to a patient. Further, the Burdick et al and Bishop warmers employ heaters that generally contact a particular portion of an article being heated, thereby heating articles in an uneven manner and enabling formation of hot spots. Moreover, the Burdick et al, Bishop, Corrigan, III et al and Van Overloop warming systems heat items simultaneously to only a single desired temperature rendering them incompatible for applications requiring various items to be heated to different temperature ranges. These systems further employ a heating element covering a substantial portion of a conducting member, thereby increasing system costs and power usage. The above described systems typically have heating area dimensions specifically configured to accommodate particular items and, therefore, are limited with respect to the types of items that may be heated by those systems. The Koopman system employs heating elements disposed within a housing cavity and not in direct contact with the surface supporting an item. This typically requires the system to heat the cavity, thereby providing increased heating time for an item to attain a particular temperature. In addition, the above-described warming systems do not provide a selectively configurable structure for partitioning system compartments to facilitate a relatively even heat distribution for additional or varying items placed therein.

The present invention overcomes the aforementioned problems and provides several advantages. For example, the present invention warming system distributes heat evenly to one or more medical items of varying shapes and sizes, thereby ensuring relatively uniform heating of items with enhanced temperature control. Further, since medical items are supported within system compartments on a heating plate, the medical items are not in direct contact with a heater, thereby avoiding creation of "hot spots". Moreover, the present invention reduces costs by utilizing a single common controller to simultaneously control each heater within system compartments, and provides versatility since each compartment heater may be individually controlled to enable the system to heat medical items contained within different compartments to the same or different desired temperatures. In addition, a warming system rack structure of the present invention provides even heat distribution and enhanced temperature regulation of individual medical items contained within the receptacles. Since most hospital personnel are unaware of the temperature of a particular medical item prior to use, the rack structure provides a fairly high degree of control of that temperature.

OBJECTS AND SUMMARY OF THE INVENTION

Accordingly, it is an object of the present invention to heat a medical item to a desired temperature by uniformly distributing heat about the medical item, thereby avoiding creation of "hot spots" and "cold spots".

It is another object of the present invention to simultaneously maintain various items at different desired temperatures for use in medical procedures.

Yet another object of the present invention is to simultaneously maintain various items at different desired temperatures for use in medical procedures via a temperature control system including heating compartments individually controlled by a common controller, wherein each heating compartment is maintained at a desired temperature.

Still another object of the present invention is to evenly distribute heat about a medical item within a heating compartment of the system by conducting heat through a heating plate that at least partially surrounds the medical item.

A further object of the present invention is to provide a collapsible rack structure within a system heating compartment to partition that compartment and facilitate a uniform distribution of heat to additional or varying items.

The aforesaid objects may be achieved individually and in combination, and it is not intended that the present invention be construed as requiring two or more of the objects to be combined unless expressly required by the claims attached hereto.

According to the present invention, a temperature control system includes a cabinet or system housing having an interior partitioned into individual heating compartments for containing medical items. Each compartment includes a heating assembly having a generally U-shaped heating plate with thermally conductive bottom and side walls, a heater, a temperature sensor and a temperature cut-out switch. The heater is typically disposed beneath the bottom wall of the heating plate and applies heat to the heating plate to heat medical items placed thereon. The U-shaped configuration of the heating plate ensures even distribution of heat applied to one or more medical items placed within the heating compartment. The system further includes a controller in communication with the heater and temperature sensor of each heating assembly, wherein the controller controls heating of each compartment based upon a user selected desired or set point temperature associated with that compartment. A collapsible rack structure may additionally be disposed within one or more compartments to form individual receptacles in those compartments for receiving and heating medical items placed therein.

The above and still further objects, features and advantages of the present invention will become apparent upon consideration of the following detailed description of specific embodiments thereof, particularly when taken in conjunction with the accompanying drawings, wherein like reference numerals in the various figures are utilized to designate like components.

DETAILED DESCRIPTION OF THE PREFERRED EMBODIMENTS

Figure 1:
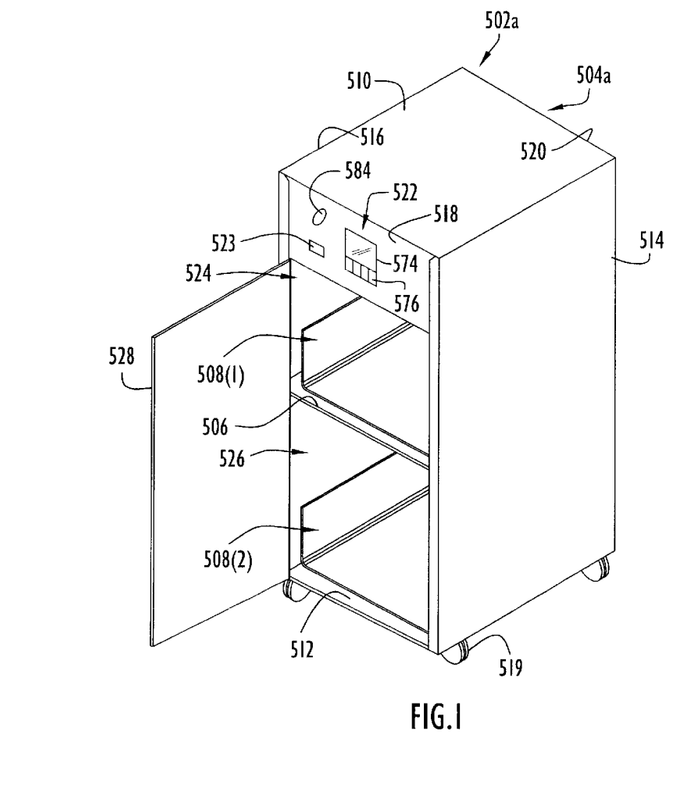
FIG. 1 is a view in perspective of a temperature controlled cabinet system in accordance with the present invention.

A temperature controlled cabinet system for heating and maintaining medical solution containers (e.g., bags or bottles containing saline or intravenous (IV) solutions, antibiotics or other drugs, blood, etc.) or other medical items (e.g., instruments) at desired temperatures is illustrated in FIG. 1. Specifically, temperature controlled cabinet system 502a includes a cabinet or system housing 504a having a shelf 506 partitioning the cabinet interior into upper and lower compartments 524, 526, respectively. Each compartment includes a respective heating assembly 508(1),508(2) for receiving medical items placed within that compartment and heating the medical items to a desired temperature. Cabinet 504a is generally in the form of a rectangular box and includes top and bottom walls 510, 512, side walls 514, 516, a front door 528, a front wall 518 disposed above the door, and rear wall 520. The cabinet walls and door are each substantially rectangular and collectively define a cabinet interior. Rollers or casters 519 are attached to the cabinet bottom wall with each caster disposed toward a corresponding cabinet bottom wall corner to enable the system to be transportable. The casters or rollers may be of any quantity, may be implemented by any conventional or other types of rollers or wheel-type structures, and may be disposed at any locations on the cabinet. Further, the cabinet may be constructed of electro-galvanized steel or other suitably sturdy material, and may be of any size or shape. However, by way of example only, the cabinet system has an approximate height of thirty-six inches. It is to be understood that the terms "top", "bottom", "side", "front", "rear", "horizontal", "vertical", "upper", "lower", "up", "down", "height", "length", "width", "depth" and the like are used herein merely to describe points of reference and do not limit the present invention to any specific orientation or configuration.

Compartments 524 and 526 are generally disposed in vertical alignment within the cabinet interior. Heating assembly 508(1) is disposed on shelf 506 within compartment 524, while heating assembly 508(2) is disposed on bottom wall 512 within compartment 526. The heating assemblies are each controlled by a common system controller 522 that enables entry of a desired or set point temperature for each heating assembly and controls heating of medical items residing within each compartment based on the associated set point temperature as described below. Controller 522 is disposed toward an intermediate section of front wall 518, while a power switch 523 is generally disposed in the front wall lower portion toward side wall 516. A fuse 584 is typically further disposed in the front wall above power switch 523, but may alternatively be disposed in rear wall 520. The power switch enables power to the controller for heating medical items placed within the compartments, while the fuse protects the cabinet from power surges. Cabinet 504a may include any quantity of compartments, rollers, shelves, power switches, controllers and accompanying control circuitry, while the cabinet components (e.g., walls, door, shelf, panels, etc.) may be arranged in any fashion.

Door 528 includes a handle (not shown) typically disposed toward an intermediate section side edge. The handle may be implemented by any conventional or other type of handle. Alternatively, the handle may be disposed on the door at any suitable location. Door 528 generally pivots toward and away from the cabinet as described below, and may be constructed of electro-galvanized steel or other suitably sturdy material. The door may include an opening covered by a substantially transparent material, such as glass or plexiglass, to serve as a window to enable viewing of the medical items and maintain heat within the cabinet. The door, opening and transparent material may be of any size or shape.

Figure 2:
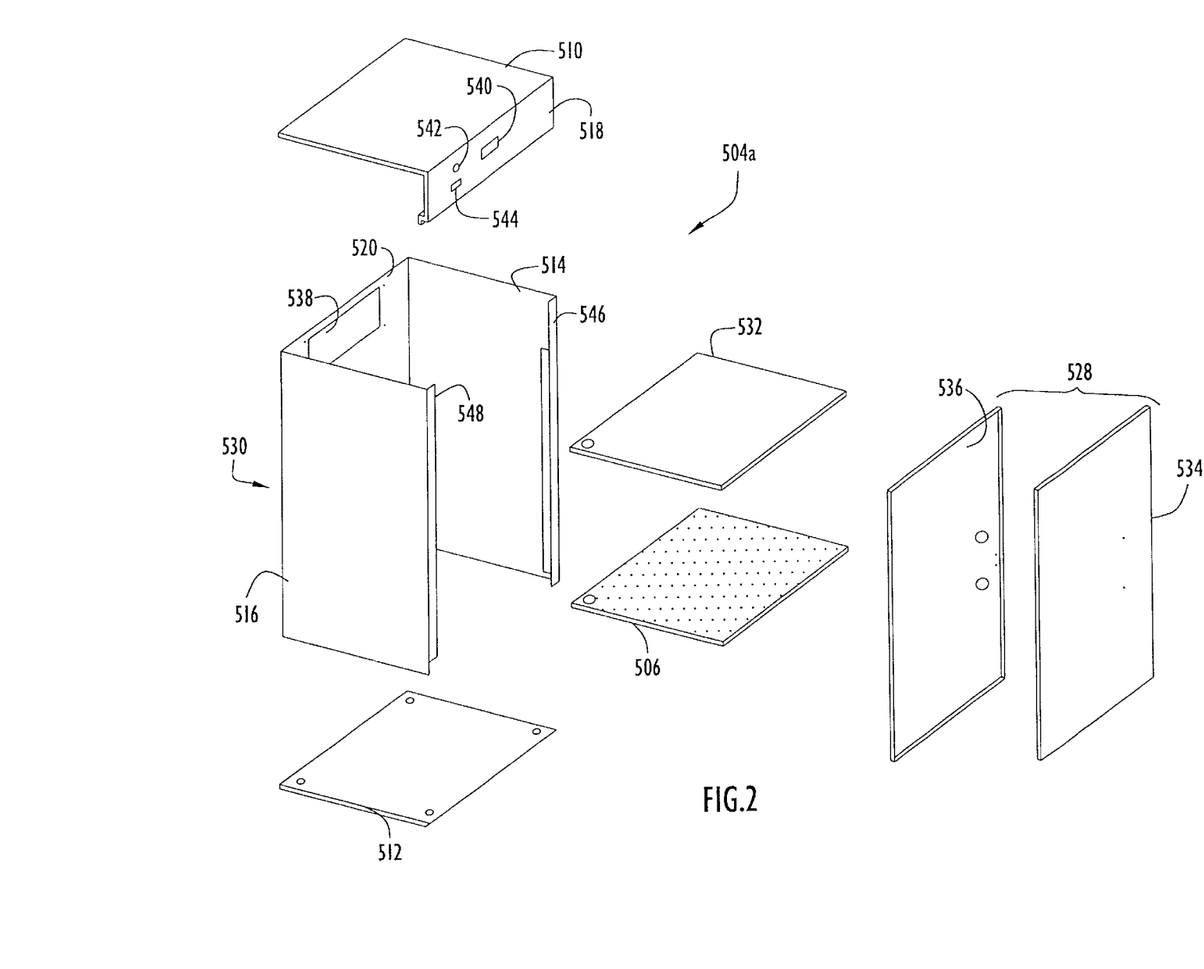
FIG. 2 is an exploded perspective view of a cabinet or housing of the system of FIG. 1.

An exemplary configuration for cabinet 504a is illustrated in FIG. 2. Specifically, cabinet 504a includes a body 530, top and bottom walls 510, 512, shelf 506 and door 528. Body 530 includes rear wall 520 interconnected to side walls 514, 516, thereby collectively defining compartment interiors. Rear wall 520 includes a substantially rectangular opening 538 defined in an upper portion thereof to permit air to cool circuitry contained within the cabinet upper portion as described below. Side walls 514, 516 each include a ledge 546, 548 defined at a side wall front edge. Ledges 546, 548 extend inwardly and substantially perpendicular to the respective side walls, and enhance interconnection of cabinet components.

A substantially rectangular cover 532 is disposed within and attached to the body slightly below the rear and side wall top edges to define a ceiling of upper compartment 524. Top wall 510 is placed over and attached to the top edges of the rear and side walls with front wall 518 extending down from the top wall front edge to the cover. The front wall includes appropriate openings 540, 542, 544 for receiving the controller, power switch, and fuse respectively. The cover and top, side, front and rear walls collectively define a chamber above compartment 524 for housing the system control circuitry described below. Opening 538 within rear wall 520 permits air to enter the chamber to cool the circuitry. The opening may be of any quantity, shape or size, and may be defined at any locations within the rear, side and front walls.

Shelf 506 is inserted within and attached to an intermediate section of the body to form compartments 524, 526 within the cabinet interior. The shelf may include multiple holes to enhance dissipation of heat within the cabinet. Door 528 includes substantially rectangular members 534, 536 each having openings defined therein for attachment of a handle (not shown). The door is attached to side wall 516 via conventional hinge mechanisms and typically pivots toward and away from the cabinet to permit access to the cabinet interior. The various cabinet components (e.g., walls, cover, shelf, door, etc.) may be of any shape or size, and may be constructed of any suitably sturdy materials. The components may be interconnected by any conventional or other fastening techniques, such as welding, molding or bending, fasteners (e.g., screws, bolts, nuts, etc.).

Figure 3:
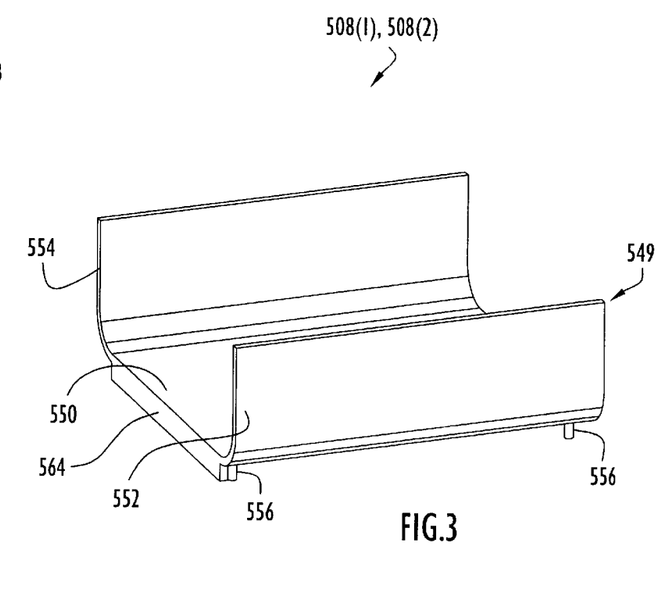
FIG. 3 is a view in perspective of a heating assembly of the system of FIG. 1.

Heating assemblies 508(1), 508(2) are each disposed within a corresponding cabinet compartment to heat medical items placed therein as described above. Each heating assembly includes an exemplary configuration as illustrated in FIG. 3. Specifically, heating assemblies 508(1), 508(2) each include a heating plate 549 having a heater 558, a temperature sensor 560 and temperature cut-out switch 562. The heating plate protects the heater from medical items (e.g., containers melting and becoming attached to the heater), and includes a thermally conductive bottom wall 550 and thermally conductive side walls 552, 554. The bottom and side walls are each generally rectangular with the side walls extending from opposing bottom wall edges and forming rounded junctions where the side wall and bottom walls meet. The side walls extend upward from the opposing bottom walls edges and generally along walls of a corresponding compartment to form a generally U-shaped heating plate configuration. The bottom wall is generally flat for receiving and containing medical items thereon and extends along the bottom of a corresponding compartment. Legs 556 are attached to the underside of bottom wall 550 with each leg disposed toward a corresponding bottom wall corner. The legs elevate the heating plate above the corresponding compartment bottom (e.g., shelf 506 for compartment 524, or bottom wall 512 for compartment 526) to prevent the heater from contacting the cabinet. The legs may be of any quantity, shape or size, and may be disposed at any suitable locations. The front portion of bottom wall 550 includes a substantially rectangular protective panel 564 extending down from a front edge of the heating plate bottom wall. The protective panel prevents users from gaining access to the heater, thereby preventing user injury.

Figure 4:
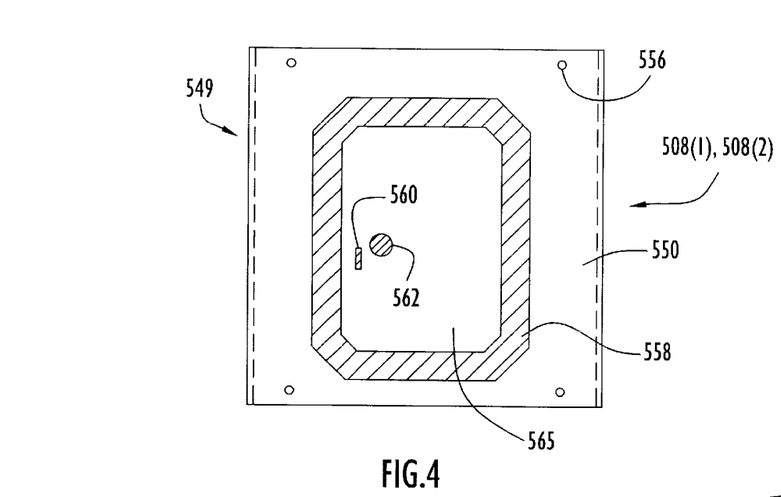
FIG. 4 is a view in plan of the underside of a heating plate of the heating assembly of FIG. 3.

Heater 558 and associated assembly components are typically disposed on the underside of bottom wall 550 as illustrated in FIG. 4. Specifically, heater 558 is disposed on the underside of the bottom wall and applies heat to the heating plate. The heat applied by the heater is conducted by the heating plate bottom and side walls to provide an even heat distribution to the medical items residing on the heating plate, thereby preventing localized heating of the medical items. Further, since the medical items are not in direct contact with the heater, this arrangement avoids creation of "hot spots". Alternatively, the heater may be disposed at any locations on the side or bottom walls of the heating plate.

The heater is preferably configured to cover only a portion of the heating plate bottom wall, and is generally rectangular having truncated corners and a generally rectangular opening 565. The heater is preferably implemented by a conventional etched foil silicon rubber heating pad, while a connector (not shown) facilitates connections for the heater. The heater further includes a pressure sensitive or other type of adhesive for attachment to the heating plate bottom wall. The heater may be of any quantity (e.g., at least one), shape, or size, and may include any configuration that covers the entirety or a portion of a corresponding heating plate bottom wall (e.g., strips, bars, segments, include various openings, etc.). In addition, the heater may be implemented by any conventional or other type of heater or heating element (e.g., heating coils) to heat the heating plate.

Temperature sensor 560 is typically disposed on the underside of the heating plate bottom wall, generally within the confines of the heater (e.g., the portion of the heater not covering the bottom wall). The temperature sensor is preferably implemented by a conventional RTD temperature sensor (e.g., 1,000 Ohm RTD) and measures the temperature of the heating plate bottom wall. However, the temperature sensor may be implemented by any conventional or other type of temperature sensor, and may be disposed at any suitable location on the heating plate or within a compartment, thereby obviating the need for an internally mounted temperature sensor on the heating element. The temperature measurement of sensor 560 is provided to the controller for control of the heater as described below. In addition, a temperature sensitive cut-out switch 562 is disposed on bottom wall 550 within the confines of the heater. The cut-out switch basically disables current to heater 558 in response to a temperature measurement exceeding a temperature threshold. In other words, the cut-out switch disables the heater in response to detection of excessive heater temperatures. The cut-out switch may be implemented by any conventional switching type or limiting devices, such as a high limit thermostat, and may be disposed at any suitable locations.

Referring back to FIG. 1, controller 522 typically includes a display 574 (e.g., LED or LCD), and a plurality of input devices or buttons 576 for enabling entry of desired or set point temperatures for the corresponding compartments. The input devices are manipulated to enable entry of the set point temperatures, while display 574 may indicate the actual temperature of each heating plate bottom wall measured by a corresponding temperature sensor 560 (FIG. 4) or the set point temperatures entered by the operator. Display 574 typically displays the measured temperature of each heating plate, and may be directed, via the input devices, to display the set point temperatures.

The heating plates of each compartment are typically heated to the same temperature, but the temperatures may be different depending upon the medical items to be heated. Since the quantity or types of medical items placed in each compartment may differ, separate heating controls for the compartments are required. Accordingly, controller 522 provides independent control for each heating assembly and essentially implements a feedback control loop to control heating of those compartments. Specifically, controller 522 includes inputs for receiving temperature signals from temperature sensor 560 of each heating assembly indicating the temperature of a corresponding heating plate bottom wall. In response to the measured temperature of a heating plate bottom wall being equal to or exceeding the set point temperature entered for a corresponding compartment, the controller disables power to the heater associated with that compartment via a solid state relay described below. Conversely, when the measured temperature of the heating plate bottom wall is below the set point temperature entered for the corresponding compartment, the controller enables power to the heater associated with that compartment via the solid state relay. The controller is generally pre-programmed with a fuzzy logic or other type of control algorithm to control each heating assembly based on the measured temperature of the corresponding heating plate bottom wall. Controller 522 is preferably implemented by a 32A Series Temperature/Process Controller manufactured by Love Controls, a Division of Dwyer Instruments, Inc. Generally, this type of controller provides single set point capability for a process, or dual set point capability (e.g., dependent high and low set points) for the same process, and displays the set point and actual or process temperatures. However, in order to employ this type of controller within the present invention, the 32A Series Controller has been slightly modified. In particular, the alarm relay and associated circuits of the 32A Series Controller have been removed to permit insertion of loop circuitry, thereby enabling independent operation of plural set points. Further, the 32A Series Controller has been modified to display the actual temperature of each heating plate, while the set point temperatures entered for the compartments may be displayed by manipulating input devices 576. In addition, the options typically available for the 32A Series Controller have not been enabled. It is to be understood that controller 522 may be implemented by any conventional or other processor or circuitry utilizing any control algorithm to control the heating assemblies, whereby controller 522 or other processor or circuitry may accommodate any quantity of heaters, compartments or set points.

Figure 5:
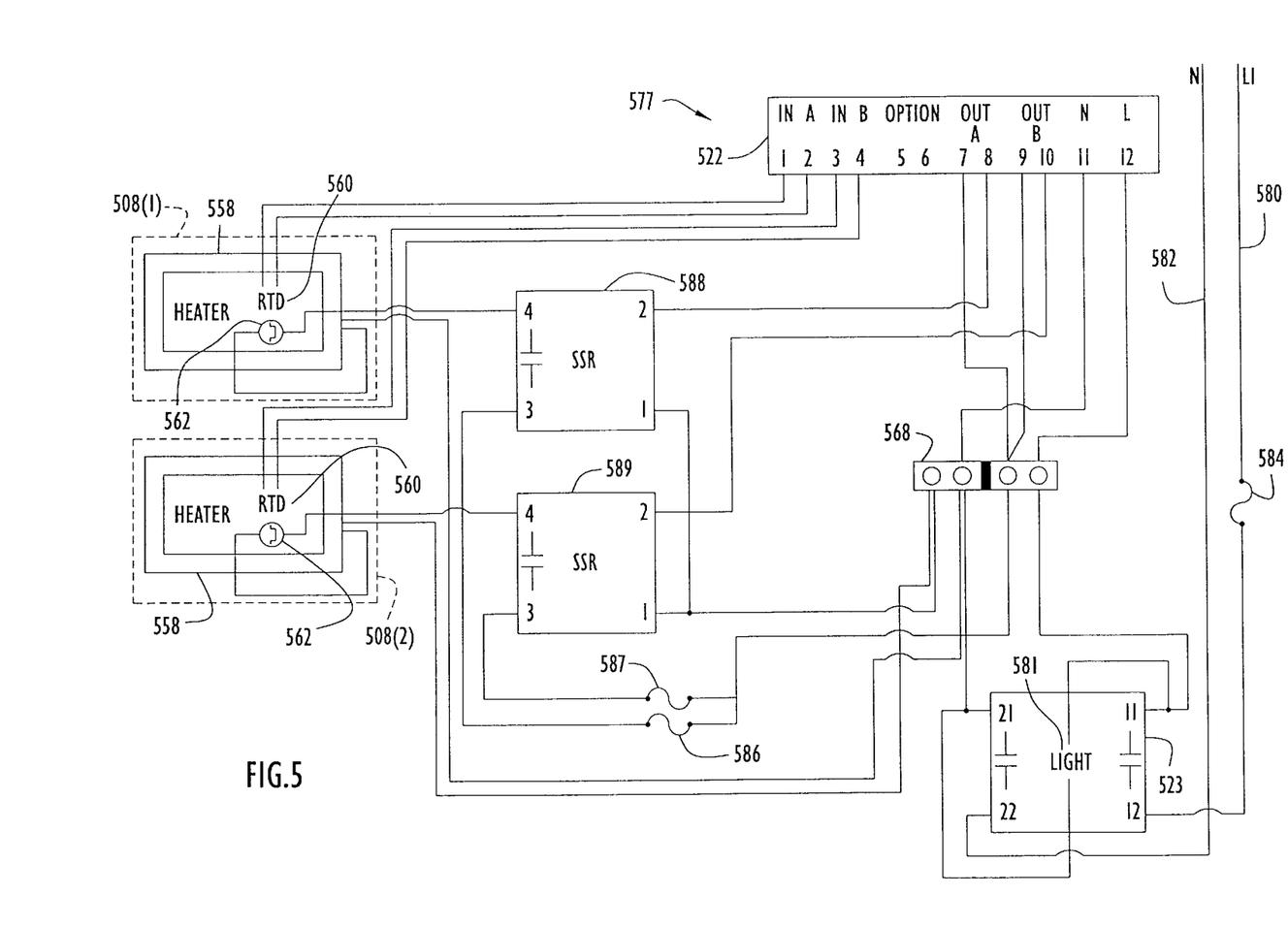
FIG. 5 is an electrical schematic diagram of an exemplary control circuit of the system of FIG. 1.

An exemplary control circuit of the temperature controlled cabinet system is illustrated in FIG. 5. Specifically, system control circuit 577 includes power conductors 580, 582, power switch 523, controller 522 and solid state relays 588, 589. The solid state relays are each associated with a corresponding heater 558 of heating assemblies 508(1), 508(2). Power conductors 580, 582 enable power to the circuit with conductor 580 typically supplying a positive potential, while conductor 582 provides a negative or reference potential. Fuse 584 is connected in series with conductor 580 to prevent power surges from damaging the circuitry. Power switch 523 is connected to conductor 580 and in series with fuse 584, and may include a light 581 to illuminate the switch. The power switch is further connected to conductor 582 and controller 522 to enable power to the controller.

Controller 522 receives power from power switch 523 and is further connected to solid state relays 588, 589 and temperature sensor 560 and heater 558 of each heating assembly 508(1), 508(2). Temperature sensor 560 of each heating assembly measures temperature of a corresponding heating plate bottom wall and transmits a signal to controller 522 indicating that temperature. The controller controls each solid state relay 588, 589 to enable or disable power to a corresponding heater 558 in response to the temperature measured for the associated heating plate as described above. The solid state relays are each connected to controller 522 and a terminal block 568 disposed between the power switch and controller, between the controller and solid state relays, and between the controller and heater of each heating assembly 508(1), 508(2). The terminal block receives wiring from the solid state relays, power switch, controller and each heating assembly heater and facilitates connections between the wiring. Fuses 586, 587 are respectively connected between solid state relays 588, 589 and the terminal block to prevent damage to the relays and corresponding heaters.

Temperature cut-out switch 562 of each heating assembly is connected between a heater 558 of that heating assembly and a corresponding solid state relay. The cut-out switch disables current to a corresponding heater in response to detecting the heater temperature in excess of a predetermined temperature threshold. Control circuit 577 may be implemented by any conventional circuitry components performing the above described functions.

Operation of the temperature controlled cabinet system is described with reference to FIGS. 1 and 5. Initially, an operator selects medical solution containers (e.g., bags or bottles containing saline or intravenous (IV) solutions, antibiotics or other drugs, blood, etc.) or other medical items (e.g., instruments) for heating within the cabinet and determines appropriate temperatures for the items. The operator subsequently enables power switch 523, whereby the operator grasps and applies force to the door handle to pivot the door outward from the cabinet interior to an open position. The medical items are disposed on any quantity (e.g., at least one) or combination of heating assemblies 508(1), 508(2) within the compartments. The door is subsequently pivoted towards the cabinet to a closed position. The desired or set point temperatures are entered into controller 522 via input devices or buttons 576. The controller receives signals from the temperature sensor of each heating assembly and determines appropriate controls for a corresponding solid state relay 588, 589 to enable or disable power to an associated heater as described above. Each heater 558 applies heat to a corresponding heating plate bottom wall, whereby the side walls of that heating plate conduct heat from the bottom wall to evenly distribute the heat to the medical items contained therein as described above.

Controller 522 displays the heating plate bottom wall temperature of each heating assembly measured by a corresponding temperature sensor 560, and may be further directed to alternatively display the set point temperature entered for the compartments based on manipulation of input devices 576. When the medical items have attained the desired temperatures, the door is pivoted to an open position as described above, whereby the heated medical items are removed from the compartments for use, while the door is subsequently returned to a closed position. Further, additional medical items may replace the removed items within the compartments for heating by the system. The medical items may be loaded into the system several hours before the items are required for use (e.g., the items may be placed within the system the night prior to use in a medical procedure) so that the items, such as intravenous (IV) solution bags, may attain their operational temperature and be available for immediate use by the required time. It is to be understood that either or both of the compartments may be used and independently controlled in substantially the same manner described above to maintain medical items at the same or different desired temperatures. Moreover, any quantity of items may be disposed within the compartments for heating by the cabinet.

Figure 6:
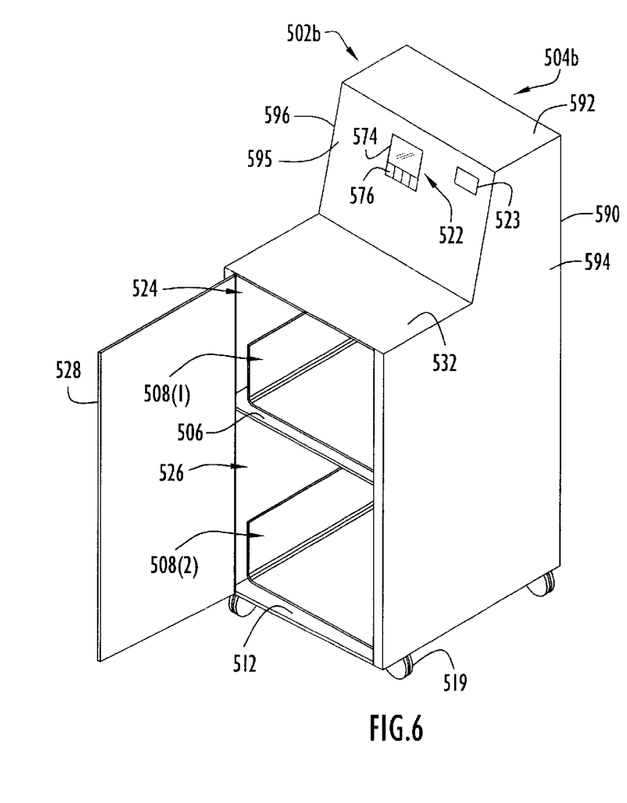
FIG. 6 is a view in perspective of an alternative cabinet or housing for the system of FIG. 1.

An alternative configuration for cabinet 504a is illustrated in FIG. 6. Cabinet 504b is substantially similar to cabinet 504a described above except that cabinet 504b includes a chamber on its top surface for housing system control circuitry. Specifically, cabinet 504b is generally in the form of a rectangular box having a raised chamber defined on its top surface. The cabinet includes front door 528, cover 532, front panel 595, bottom and rear walls 512, 590, side walls 594, 596 and top panel 592. The cabinet front door, cover and bottom wall are each as described above, while the cabinet front door, cover and bottom and side walls collectively define the cabinet interior. Shelf 506 is disposed within the cabinet interior at an intermediate cabinet section to partition the cabinet interior into upper and lower compartments 524, 526 as described above. Each compartment includes a respective heating assembly 508(1), 508(2) for receiving and heating medical items placed thereon in substantially the same manner described above.

Front panel 595 is substantially rectangular and is attached to and extends upward from an intermediate section of cover 532. The front panel is tilted slightly rearward and has a longer dimension similar to the transverse dimension of cover 532. Rear wall 590 is substantially rectangular and is attached to side walls 594, 596, cover 532 and bottom wall 512. The rear wall extends from the bottom wall toward the upper edge of front panel 595. Top panel 592 is substantially rectangular and is attached to and disposed between the upper edges of the front panel and rear wall. Side walls 594, 596 are generally rectangular and are attached to and extend between the bottom wall and cover. The side walls partially extend beyond the cover for attachment to top panel 592, and are further attached to and disposed between the front panel and rear wall. The top panel, front panel, cover and side and rear walls collectively define a chamber on the cover top surface to house the system circuitry. Front panel 595 further includes controller 522 disposed toward a front panel central portion and power switch 523 disposed toward a front panel upper edge near side wall 594. Fuse 584 (not shown) is typically disposed on rear wall 590. System 502b functions in substantially the same manner described above for system 502a to heat items placed therein.

Figure 7A:
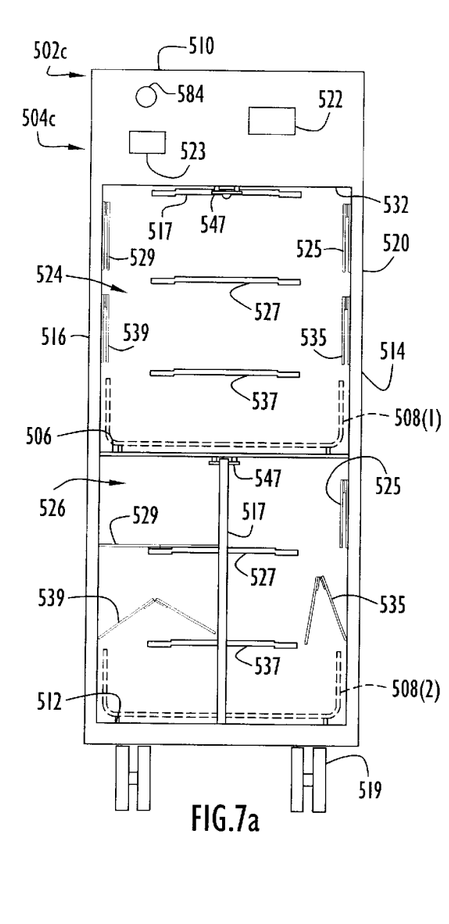
FIG. 7a is a view in elevation of the system of FIG. 1 including collapsible rack structures for containing medical items, the rack structures being illustrated in fully and partially collapsed states.
Figure 7B:
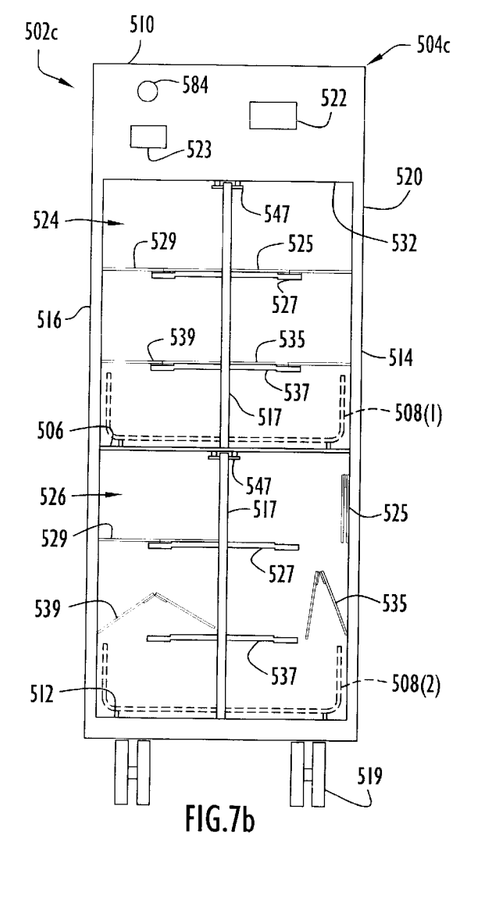
FIG. 7b is a view in elevation of the system of FIG. 7a with the rack structures in fully and partially expanded states.

In addition, the cabinet systems described above may further include a collapsible rack structure disposed within the cabinet compartments to contain items as illustrated, by way of example only, in FIGS. 7a–7b. System 502c is substantially similar to system 502a described above for FIGS. 1–5, and further includes a collapsible rack structure. Specifically, compartments 524, 526 each include a series of supports 527, 537 disposed on the interior surface of rear wall 520. The supports are substantially rectangular having a narrow transverse or shorter dimension to essentially form ledges within each compartment protruding from the rear wall. The supports extend substantially in parallel and are vertically spaced from each other a slight distance.

Upper leaves 525, 529 are disposed within each compartment 524, 526 and are attached to side walls 514, 516, respectively, with a corresponding support 527 disposed between those leaves. Similarly, lower leaves 535, 539 are disposed within each compartment 524,526 and are attached to side walls 514,516, respectively, below leaves 525, 529 with a corresponding support 537 disposed between the lower leaves. Each upper and lower leaf includes a pair of substantially rectangular board members attached to each other by a hinge type mechanism, thereby permitting each leaf to be folded and placed against the cabinet side wall.

Each compartment 524, 526 includes a divider bar 517 and a bar holder 547. Bar holder 547 may be implemented by any conventional or other securing or clasping mechanism and secures the bar within each compartment. Bar holder 547 within compartment 524 is attached to the underside of cover 532, while the bar holder within compartment 526 is attached to the underside of shelf 506. However, the bar holders may be of any quantity, shape or size, and may be disposed in any suitable locations. Bar 517 includes a plurality of hinged sections that enable the bar to expand and collapse or fold for storage within a corresponding bar holder (FIG. 7a). Bar 517 includes a narrow transverse or shorter dimension, and is attached to a corresponding holder within each compartment 524, 526. When in an expanded state, the bar extends down from a corresponding holder within a compartment toward the front of the cabinet. The bar essentially provides a vertical divider toward the front portion of each compartment that is generally perpendicular to the unfolded leaves, and the bar includes ledges (not shown) disposed coincident supports 527, 537 within that compartment. The bar ledges and rear wall supports within a compartment provide support for the upper and lower leaves of that compartment, thereby forming individual receptacles. Heating assemblies 508(1), 508(2) are respectively disposed on the shelf and bottom wall within compartments 524, 526 to heat medical items placed in the compartments as described above. The side walls of each heating plate typically extend from the heating plate bottom wall to a point slightly below respective supports 537 and lower leaves 535, 539 to enable the rack structure to accommodate the heating assemblies. Alternatively, the upper and lower leaves within a compartment may be connected to the side walls of the heating plate of a corresponding heating assembly to form the rack structure.

The rack structure may be utilized within a compartment by extending bar 517 down from holder 547. The bar ledges and rear wall supports provide support for the distal portions of the upper and lower leaves as described above. Each upper and lower leaf may be unfolded and placed on a corresponding rear wall support and bar ledge to form individual receptacles within the compartment. Medical items may be placed in one or more of the receptacles for heating. The rack structure provides an even heat distribution from the heating assembly to the individual medical items placed within the receptacles. A convective flow of heat is developed around the medical items supported in the rack structure, and the system may further include a fan to enhance this flow and provide forced air convection. In order to collapse the rack, the upper and lower leaves are folded and placed against the compartment side walls, while the bar is collapsed and placed in the bar holder.

Any portion of the rack structure may be utilized within a compartment to heat medical items. For example, the bar and upper and lower leaves within a compartment may remain in their collapsed states, and medical items may be placed on the heating assembly for heating as described above (e.g., compartment 524 as shown in FIG. 7a). Conversely, a bar may be extended within a compartment with each upper and lower leaf of that compartment unfolded to form several receptacles for heating items (e.g., compartment 524 as shown in FIG. 7b). In addition, a bar may be extended within a compartment with some of the upper and lower leaves of that compartment unfolded to form receptacles to heat items, while additional items may be placed on the heating assembly for heating as described above (e.g., compartment 526 as shown in FIGS. 7a–7b). Any portion of the rack structure within any compartment may be expanded for use as described above. The rack structure components (e.g., supports, leaves, bar, bar holder, etc.) may be of any shape or size, and may be constructed of any suitable materials (e.g., conductive or non-conductive materials, such as plastic coated wiring, metal bars or rods, etc.). The rack structure may include any quantity of components (e.g., supports, leaves, bars, bar holders, etc.) of any shape or size to partition a compartment into any quantity of receptacles. The receptacles may be of any shape or size and may contain any quantity of medical items. In addition, the rack structure may be utilized in any of the cabinet systems described above, and may be implemented by any structures or devices partitioning compartment interiors into individual receptacles. For example, a pre-formed rack may be placed within the compartments to contain medical items for heating.

It will be appreciated that the embodiments described above and illustrated in the drawings represent only a few of the many ways of implementing a temperature controlled cabinet system and method for heating items to desired temperatures.

The present invention systems may be of any shape or size and may be constructed of any suitable materials. The systems may include any quantity (e.g., at least one) of compartments having any shape or size and located within the housing at any suitable locations. The housing body components (e.g., walls, shelves, door, panels, etc.) of the systems may be of any shape or size, may be constructed of any suitable materials and may be interconnected via any conventional or other attachment techniques (e.g., welding, fasteners, constructed as an integral unit, etc.). The systems may warm any quantity of any types of medical or other items, where the items may be placed within any quantity or combination of compartments. The systems generally heat medical items to a normal body temperature in the approximate of 86° F.–104° F., however the systems may heat any types of items to any desired temperatures.

The controller of the systems may be implemented by any conventional or other microprocessor, controller or circuitry performing the functions described above. The controller may be disposed on or within the systems at any suitable location. The controller may control the heaters to any desired temperatures. The controller may include any quantity of any type of input device (e.g., keys, buttons, mouse, voice, etc.) to facilitate entry of desired temperatures. The controller may include any type of display of any shape or size to convey any desired information. The display may be integral with or detached from the controller or systems. The systems may include any quantity of controllers, while the controller may control heating of any quantity of compartments or heating assemblies. The controller may utilize any conventional or other control algorithms (e.g., fuzzy logic, PID, etc.).

The door may be of any shape or size, may be constructed of any suitable materials, and may pivot in any desired direction via any conventional or other pivoting or hinged mechanisms to facilitate placement and removal of items within the systems. Further, the door may include a window of any size or shape having any type of partially or fully opaque, translucent or transparent material. The door may include any quantity of any type of handle disposed at any suitable locations.

The heating plate of the heating assembly may be of any configuration that surrounds the medical items placed within the system. The plate may be of any shape or size, may include any quantity of conducting and/or non-conducting walls and may be constructed of any suitable materials. The bottom and side walls may be of any shape, while the side walls may extend at any angle for any desired distance. The plate may include any quantity of legs disposed at any suitable locations. The legs may be of any shape or size and may be constructed of any suitable materials. Alternatively, the heating plate may be elevated from a compartment floor by any conventional or other techniques (e.g., suspended or affixed to compartment walls, etc.). The protective plate may be of any size or shape, may be constructed of any suitable materials, and may be disposed at any location to prevent a user from contacting the heater. The heating assembly may be utilized with or without the protective plate.

The heater may be implemented by any conventional heater or other heating device. The heating plate may include any quantity of heaters arranged in any configurations (e.g., strips, annular, segments, etc.) and disposed at any suitable locations for applying heat. The heater may be attached to the heating plate via any conventional or other fastening techniques (e.g., pressure sensitive or other adhesives, etc.). The systems may alternatively include any quantity of heaters disposed at any suitable locations within or proximate a compartment.

The temperature sensor may be implemented by any conventional or other temperature measuring device (e.g., RTD, infrared, etc.) and be disposed at any suitable location on the heating plate or within or proximate a compartment. The cut-out switch may be implemented by any conventional or other limiting device and may be set to function at any desired temperature. The cut-out switch may be disposed at any location on the heating plate or within or proximate a compartment. The heater and other circuitry may utilize any conventional or other connectors or wiring to transfer power and other signals to system components. Further, the power switch, relays, fuses, terminal block and other control circuit components may be implemented by any conventional or other electrical components performing the functions described above. The circuit may be disposed at any location and arranged in any fashion to control heating of the compartments as described above. Moreover, the control circuit may include any type of components to perform the functions described above. The power switch, fuse and controller may be disposed and arranged in any fashion on the housings of the systems.

The rack structure of the present invention may be of any shape or size, may be constructed of any suitable materials and may be configured to include any quantity of receptacles . The rack structure may include any quantity of leaves and supports of any size and shape, constructed of any suitable materials and disposed at any suitable locations. The leaves may include any conventional or other folding or collapsing mechanisms (e.g., hinges, etc.) and may collapse or fold in any fashion. Alternatively, the leaves may each be non-folding (e.g., unable to be folded or collapsed) and pivot toward and away from compartment walls to provide a selective configuration. Further, the leaves may be attached to the heating plate at any suitable locations via any conventional or other fastening techniques. The rack structure may be an independent unit and may be removably disposed within a system compartment. The divider bars and bar holders may be of any quantity, size and shape and may be disposed at any location within a system compartment. The divider bars may be collapsible via any conventional or other techniques (e.g., hinges or other folding or collapsing mechanisms, etc.) and may collapse or fold in any fashion. The bar holder may include any conventional or other securing mechanism (e.g., bracket, clasp, etc.) for receiving and securing a divider bar. The rack structure may include any quantity of receptacles of any shape or size for containing any quantity of any type of medical or other items. The rack structure may be selectively configured to form any quantity of receptacles where any quantity of leaves may be manipulated in any combination to form those receptacles.

The present invention systems may be used at any suitable location (e.g., hospital or other medical facility, emergency medical or other vehicles, etc.) to heat any quantity of any type of medical or other items. The systems may be transportable and include any quantity of any type of rollers or casters disposed at any suitable locations. In addition, medical or other equipment (e.g., IV pole, light, etc.) may be disposed on the top or other surfaces of the systems to enhance system capabilities.

It is to be understood that the present invention is not limited to the specific configurations or applications described above, but may be implemented by any system including independently controlled compartments that evenly distribute heat from a heat source to various types of medical or other items.

From the foregoing description it will be appreciated that the invention makes available a novel temperature controlled cabinet system and method for heating items to desired temperatures wherein a system housing includes at least one compartment having a heating assembly with a generally U-shaped heating plate to evenly distribute heat to items placed therein.

Having described preferred embodiments of a new and improved temperature controlled cabinet system and method for heating items to desired temperatures, it is believed that other modifications, variations and changes will be suggested to those skilled in the art in view of the teachings set forth herein. It is therefore to be understood that all such variations, modifications and changes are believed to fall within the scope of the present invention as defined by the appended claims.

What is claimed is:

1. A temperature control system for heating medical items to desired temperatures comprising:
   a system housing;
   a heating compartment disposed within said housing to receive at least one medical item;
   a heating assembly disposed within said heating compartment to heat said compartment and said at least one medical item contained in that compartment, wherein said heating assembly includes:
      a heating plate to receive said at least one medical item thereon and to distribute heat within said compartment and to said at least one medical item;
      a heater affixed and applying heat to said heating plate; and
      a temperature sensor to measure a temperature of said heating plate; and
   a controller to facilitate entry of a desired temperature and to control a thermal output of said heater to heat at least one medical item to said entered desired temperature based on said temperature measured by said temperature sensor;
   wherein said heating plate includes a medical item support platform to support at least one medical item within said heating compartment and a plurality of secondary conducting walls and said heater is attached to and covers selected portions of said medical item support platform to directly apply heat to said medical item support platform; and
   wherein said secondary conducting walls are attached to said medical item support platform at locations outside said selected portions and receive said applied heat through conduction from said medical item support platform, and wherein said medical item support platform and said secondary conducting walls distribute heat in a substantially uniform manner to said at least one medical item disposed between said secondary conducting walls.

2. The temperature control system of claim 1, wherein said heating plate has a generally U-shaped configuration with said medical item support platform including a thermally conductive bottom wall and said secondary conducting walls including two thermally conductive side walls extending from said bottom wall, and wherein said heater is affixed to said bottom wall.

3. The temperature control system of claim 2, wherein said heater is affixed to an underside of said bottom wall.

4. The temperature control system of claim 1, wherein said heating plate includes a protective panel covering at least a portion of said heater to prevent contact between a user and said heater.

5. The temperature control system of claim 1, wherein said heating compartment includes a compartment bottom wall configured to receive said heating assembly, and said heating assembly includes a plurality of legs affixed to the underside of said heating plate to elevate and support said heating plate above said compartment bottom wall.

6. The temperature control system of claim 1, wherein said heating assembly includes a temperature sensitive switch in communication with said heater, wherein said switch is configured to disable said heater upon measurement of a heater plate temperature in excess of a threshold temperature.

7. The temperature control system of claim 1, wherein said controller enables said heater to heat said heating plate in response to said temperature measured by said temperature sensor being below said entered desired temperature and disables said heater in response to said temperature measured by said temperature sensor being at or exceeding said entered desired temperature.

8. The temperature control system of claim 1, wherein said controller facilitates entry of said desired temperature via a user input device communicating with said controller.

9. The temperature control system of claim 1, wherein said system includes a plurality of heating compartments each having a corresponding heating assembly, and wherein said controller facilitates entry of a plurality of desired temperatures each associated with a corresponding heating compartment, wherein said controller independently controls said heating assemblies to heat said compartments to their corresponding desired temperatures.

10. The temperature control system of claim 1, further comprising:
    a selectively configurable rack structure to partition said compartment into at least one receptacle for receiving said at least one medical item, wherein said rack structure facilitates even heat distribution within said compartment and to said at least one medical item placed therein.

11. The temperature control system of claim 10, wherein said rack structure includes at least one support affixed to a first wall of said heating compartment and a plurality of platform members attached to a second wall of said heating compartment and configured to selectively extend toward said at least one support to form said at least one receptacle for receiving said at least one medical item.

12. A temperature control system for heating medical items to desired temperatures comprising:
    a system housing;
    a plurality of heating compartments disposed within said housing to receive at least one medical item;
    a plurality of heating assemblies each disposed within a corresponding heating compartment to heat that compartment and said at least one medical item contained in that compartment, wherein each said heating assembly includes:
        a heating plate including a medical item support platform to receive and support at least one medical item thereon and to distribute heat within that compartment and to said at least one medical item contained therein;
        a heater affixed and applying heat to said heating plate; and
        a temperature sensor to measure a temperature of said heating plate; and
    a controller to facilitate entry of desired temperatures for said heating compartments and to independently control a thermal output of each said heater to heat said at least one medical item contained within a corresponding compartment to said entered desired temperature associated with that compartment based on said temperature measured by a corresponding temperature sensor;
    wherein said controller controls said heating assemblies to heat at least two of said compartments to different desired temperatures.

13. A temperature control system for heating items to desired temperatures comprising:
    a system housing;
    a heating compartment disposed within said housing to receive at least one item;
    a heating assembly disposed within said heating compartment to heat said compartment and said at least one item contained in that compartment, wherein said heating assembly includes:
        a heating plate to distribute heat within said compartment and to said at least one item;
        a heater applying heat to said heating plate; and
        a temperature sensor to measure a temperature of said heating plate;
    a controller to facilitate entry of a desired temperature and to control a thermal output of said heater to heat said at least one item to said entered desired temperature based on said temperature measured by said temperature sensor; and
    a selectively configurable rack structure to partition said compartment into at least one receptacle for receiving said at least one item.

14. The system of claim 13 wherein said rack structure facilitates even heat distribution within said compartment and to said at least one item placed therein.

15. The temperature control system of claim 13, wherein said rack structure includes at least one support affixed to a first wall of said heating compartment and a plurality of platform members attached to a second wall of said heating compartment and configured to selectively extend toward said at least one support to form said at least one receptacle for receiving said at least one item.

16. The temperature control system of claim 13, wherein said system housing includes a plurality of heating compartments and each compartment includes a corresponding rack structure.

17. In a temperature control system having a system housing, a heating compartment disposed within the housing, a heating assembly disposed within the heating compartment and including a heating plate, a heater and a temperature sensor, and a controller for controlling the heating assembly, wherein said heating plate includes a first wall and a plurality of secondary conducting walls, a method of heating medical items to desired temperatures comprising the steps of:
    (a) receiving at least one medical item on said heating plate within said compartment;
    (b) facilitating entry of a desired temperature for said compartment via said controller;
    (c) applying heat directly to said first wall of said heating plate via said heater attached to and covering selected portions of said first wall;
    (d) conducting said applied heat from said first wall via said secondary walls to distribute heat in a substantially uniform manner to said at least one medical item disposed between said secondary walls, wherein said secondary conducting walls are attached to said first wall at locations outside said selected portions;
    (e) measuring a temperature of said heating plate via said temperature sensor; and
    (f) controlling a thermal output of said heater via said controller to heat said at least one medical item to said entered desired temperature based on said temperature measured by said temperature sensor.

18. The method claim 17, wherein said heating plate has a generally U-shaped configuration with said first wall including a thermally conductive bottom wall and said secondary walls including two thermally conductive side walls extending from said bottom wall and said heater is affixed to said bottom wall, and wherein step (d) further includes:
(d.1) conducting said applied heat from said bottom wall via said side walls to distribute heat in a substantially uniform manner to said at least one medical item disposed between said side walls.

19. The method of claim 17, wherein said heating plate includes a protective panel covering at least a portion of said heater, and step (a) further includes:
(a.1) preventing contact between a user and said heater via said protective panel.

20. The method of claim 17, wherein said heating compartment includes a compartment bottom wall configured to receive said heating assembly, and said heating assembly includes a plurality of legs affixed to the underside of said heating plate, wherein step (a) further includes:
(a.1) elevating and supporting said heating plate above said compartment bottom wall via said legs.

21. The method of claim 17, wherein said heating assembly includes a temperature sensitive switch in communication with said heater, and step (f) further includes:
(f.1) disabling said heater via said switch upon measurement of a heater plate temperature in excess of a threshold temperature.

22. The method of claim 17, wherein step (f) includes:
(f.1) enabling said heater to heat said heating plate in response to said temperature measured by said temperature sensor being below said entered desired temperature; and
(f.2) disabling said heater in response to said temperature measured by said temperature sensor being at or exceeding said entered desired temperature.

23. The method of claim 17, wherein step (b) further includes:
(b.1) facilitating entry of said desired temperature via a user input device communicating with said controller.

24. The method of claim 17, wherein said system includes a plurality of heating compartments each having a corresponding heating assembly, and step (a) further includes:
(a.1) receiving at least one medical item on said heating plates within said compartments;
step (b) further includes:
(b.1) facilitating entry of a plurality of desired temperatures each associated with a corresponding heating compartment;
step (c) further includes:
(c.1) applying heat directly to said first walls of said heating plates via said corresponding heaters attached to and covering selected portions of said first walls;
step (d) further includes:
(d.1) conducting said applied heat from said first walls of said heating plates via corresponding secondary walls to distribute heat in a substantially uniform manner to said at least one medical item disposed within said compartments between said secondary walls of said heating plates, wherein said secondary conducting walls of said heating plates are attached to corresponding first walls at locations outside said selected portions;
step (e) further includes:
(e) measuring a temperature of each said heating plate via a corresponding temperature sensor; and
step (f) further includes:
(f.1) independently controlling each said heating assembly via said controller to heat an associated compartment to a corresponding desired temperature based on a temperature measured by a corresponding temperature sensor.

25. The method of claim 17 wherein said system further includes a selectively configurable rack structure, and step (a) further includes:
(a.1) partitioning said compartment via said rack structure into at least one receptacle for receiving said at least one medical item; and
step (d) further includes:
(d.1) facilitating even heat distribution within said compartment and to said at least one medical item placed therein via said rack structure.

26. The method of claim 25, wherein said rack structure includes at least one support affixed to a first wall of said heating compartment and a plurality of platform members attached to a second wall of said heating compartment, and step (a.1) further includes:
(a.1.1) selectively extending said platform members toward said at least one support to form said at least one receptacle for receiving said at least one medical item.

27. In a temperature control system having a system housing, a plurality of heating compartments disposed within said housing, a plurality of heating assemblies each disposed within a corresponding heating compartment and including a heating plate, a heater and a temperature sensor, and a controller for controlling said heating assemblies, a method of heating medical items to desired temperatures comprising the steps of:
(a) receiving at least one medical item on said heating plates within said compartments;
(b) facilitating entry of a plurality of desired temperatures each associated with a corresponding compartment via said controller;
(c) applying heat to said heating plates via a corresponding heater;
(d) measuring a temperature of each said heating plate via a corresponding temperature sensor; and
(e) independently controlling a thermal output of each said heater via said controller to heat said at least one medical item contained within a corresponding compartment to said entered desired temperature associated with that compartment based on said temperature measured by a corresponding temperature sensor, wherein said heating assemblies are controlled to heat at least two of said compartments to different desired temperatures.

28. In a temperature control system having a system housing, a heating compartment disposed within the housing, a heating assembly disposed within the heating compartment and including a heating plate, a heater and a temperature sensor, and a controller for controlling the heating assembly, a method of heating medical items to desired temperatures comprising the steps of:
(a) partitioning said compartment into at least one receptacle via a selectively configurable rack structure to receive at least one item within said compartment;
(b) facilitating entry of a desired temperature for said compartment via said controller;

(c) applying heat to said heating plate via said heater;

(d) measuring a temperature of said heating plate via said temperature sensor; and (e) controlling a thermal output of said heater via said controller to heat said at least one item to said entered desired temperature based on said temperature measured by said temperature sensor.

29. The method of claim 28 wherein step (c) further includes:

(c.1) facilitating even heat distribution within said compartment and to said at least one item placed therein via said rack structure.

30. The method of claim 28, wherein said rack structure includes at least one support affixed to a first wall of said heating compartment and a plurality of platform members attached to a second wall of said heating compartment, and step (a) further includes:

(a.1) selectively extending said platform members toward said at least one support to form said at least one receptacle for receiving said at least one item.

31. The method of claim 28, wherein said system housing includes a plurality of heating compartments with each compartment including a corresponding heating assembly and rack structure, and step (a) further includes:

(a.1) partitioning each said compartment into at least one receptacle via a corresponding rack structure to receive at least one item within that compartment;

step (b) further includes:

(b.1) facilitating entry of a plurality of desired temperatures each associated with a corresponding compartment via said controller;

step (c) further includes:

(c.1) applying heat to each said heating plate via a corresponding heater;

step (d) further includes:

(d.1) measuring a temperature of each said heating plate via a corresponding temperature sensor; and step (e) further includes:

(e.1) independently controlling a thermal output of each said heater via said controller to heat said at least one item contained within a corresponding compartment to said entered desired temperature associated with that compartment based on said temperature measured by a corresponding temperature sensor.

32. A temperature control system for heating items to desired temperatures comprising:

a system housing;

a plurality of heating compartments disposed within said housing each for receiving at least one item;

a plurality of heating assemblies each disposed within a corresponding heating compartment to heat that compartment and said at least one item contained therein; and a controller to facilitate entry of a desired temperature for each heating compartment and to independently control a thermal output of each said heating assembly to heat said at least one item contained within a corresponding compartment to said entered desired temperature associated with that compartment;

wherein said controller controls said heating assemblies to heat at least two of said compartments to different desired temperatures.

33. In a temperature control system including a system housing, a plurality of heating compartments each disposed within said housing to receive at least one item, a plurality of heating assemblies each disposed within a corresponding heating compartment, and a controller for controlling said heating assemblies, a method of heating items to desired temperatures comprising the steps of:

(a) facilitating entry of a desired temperature for each heating compartment via said controller; and (b) independently controlling a thermal output of each said heating assembly, via said controller, to heat said at least one item contained within a corresponding heating compartment to said entered desired temperature associated with that heating compartment, wherein said heating assemblies are controlled to heat at least two of said heating compartments to different desired temperatures.

34. A temperature control system for heating medical items to desired temperatures comprising:

a system housing;

a heating compartment disposed within said housing to receive at least one medical item;

a heating assembly disposed within said compartment to heat said compartment and said at least one medical item contained in said compartment, wherein said heating assembly includes:

a heating plate to receive said at least one medical item thereon and to distribute heat within said compartment and to said at least one medical item;

a heater affixed and applying heat to said heating plate; and a temperature sensor to measure a temperature of said heating plate; and a controller to facilitate entry of a desired temperature and to control a thermal output of said heater to heat at least one medical item to said entered desired temperature based on said temperature measured by said temperature sensor;

wherein said heating plate includes at least one primary conducting wall and a plurality of secondary conducting walls, at least one of said at least one primary conducting wall and said secondary conducting walls includes a medical item support platform to support at least one medical item within said heating compartment, and said heater is attached to and covers a selected portion of said at least one primary conducting wall to directly apply heat to said selected portions; and wherein at least one of said secondary conducting walls is coupled to said at least one primary conducting wall at a location separate from said selected portion and receives said applied heat through conduction from said at least one primary conducting wall.

35. The temperature control system of claim 34, wherein said heating plate has a generally U-shaped configuration with a bottom conducting wall and side conducting walls extending from said bottom conducting wall, and said medical item support platform is disposed at said bottom conducting wall.

36. The temperature control system of claim 34, wherein said controller enables said heater to heat said heating plate in response to said temperature measured by said temperature sensor being below said entered desired temperature and disables said heater in response to said temperature measured by said temperature sensor being at or exceeding said entered desired temperature.

37. The temperature control system of claim 34, wherein said system includes a plurality of heating compartments each having a corresponding heating assembly, and wherein said controller facilitates entry of a plurality of desired temperatures each associated with a corresponding heating compartment, wherein said controller independently controls said heating assemblies to heat said compartments to their corresponding desired temperatures.

38. The temperature control system of claim 34, further comprising:

a selectively configurable rack structure to partition said compartment into at least one receptacle for receiving said at least one medical item, wherein said rack structure facilitates even heat distribution within said compartment and to said at least one medical item placed therein.

39. In a temperature control system having a system housing, a heating compartment disposed within the housing, a heating assembly disposed within the heating compartment and including a heating plate, a heater and a temperature sensor, and a controller for controlling the heating assembly, wherein said heating plate includes at least one primary conducting wall and a plurality of secondary conducting walls, a method of heating medical items to desired temperatures comprising the steps of:

(a) receiving at least one medical item on said heating plate within said compartment;

(b) facilitating entry of a desired temperature for said compartment via said controller;

(c) applying heat directly to said at least one primary conducting wall of said heating plate via said heater attached to and covering a selected portion of said at least one primary conducting wall;

(d) conducting said applied heat from said at least one primary conducting wall to at least one secondary conducting wall coupled to said at least one primary conducting wall at a location separate from said selected portion to distribute heat in a substantially uniform manner to said at least one medical item disposed on said heating plate;

(e) measuring a temperature of said heating plate via said temperature sensor; and (f) controlling a thermal output of said heater via said controller to heat said at least one medical item to said entered desired temperature based on said temperature measured by said temperature sensor.

40. The method claim 39, wherein said heating plate has a generally U-shaped configuration with a bottom conducting wall and side conducting walls extending from said bottom conducting wall, and said at least one primary conducting wall includes at least one of said bottom conducting and side conducting walls, and wherein step (d) further includes:

(d.1) conducting said applied heat from at least one of said bottom and side conducting walls via at least another of said bottom and side conducting walls to distribute heat in a substantially uniform manner to said at least one medical item disposed on said heating plate.

41. The method of claim 39, wherein step (f) includes:

(f.1) enabling said heater to heat said heating plate in response to said temperature measured by said temperature sensor being below said entered desired temperature; and (f.2) disabling said heater in response to said temperature measured by said temperature sensor being at or exceeding said entered desired temperature.

42. The method of claim 39, wherein said system includes a plurality of heating compartments each having a corresponding heating assembly, and step (a) further includes:

(a.1) receiving at least one medical item on said heating plates within said compartments;

step (b) further includes:

(b.1) facilitating entry of a plurality of desired temperatures each associated with a corresponding heating compartment;

step (c) further includes:

(c.1) applying heat directly to said at least one primary conducting wall of each of said heating plates via said corresponding heaters attached to and covering said selected portions of each of said at least one primary conducting wall;

step (d) further includes:

(d.1) conducting said applied heat from said at least one primary conducting wall of each of said heating plates to a corresponding at least one secondary conducting wall coupled to said at least one primary conducting wall at a location separate from a corresponding selected portion of said at least one primary conducting wall to distribute heat in a substantially uniform manner to said at least one medical item disposed on said heating plate;

step (e) further includes:

(e.1) measuring a temperature of each said heating plate via a corresponding temperature sensor; and step (f) further includes:

(f.1) independently controlling each said heating assembly via said controller to heat an associated compartment to a corresponding desired temperature based on a temperature measured by a corresponding temperature sensor.

43. The method of claim 39, wherein said system further includes a selectively configurable rack structure, and step (a) further includes:

(a.1) partitioning said compartment via said rack structure into at least one receptacle for receiving said at least one medical item; and step (d) further includes:

(d.1) facilitating even heat distribution within said compartment and to said at least one medical item placed therein via said rack structure.

\* \* \* \* \*

(12) EX PARTE REEXAMINATION CERTIFICATE (7484th)
United States Patent
Faries, Jr. et al.

(10) Number: US 6,384,380 C1
(45) Certificate Issued: May 4, 2010

(54) TEMPERATURE CONTROLLED CABINET SYSTEM AND METHOD FOR HEATING ITEMS TO DESIRED TEMPERATURES

(75) Inventors: Durward I. Faries, Jr., McLean, VA (US); Bruce R. Heymann, Vienna, VA (US); Calvin Blankenship, Centreville, VA (US)

(73) Assignee: Medical Solutions, Inc., Chantilly, VA (US)

Reexamination Request:
No. 90/009,423, Jun. 2, 2009

Reexamination Certificate for:
Patent No.: 6,384,380
Issued: May 7, 2002
Appl. No.: 09/684,863
Filed: Oct. 6, 2000

Related U.S. Application Data
(60) Provisional application No. 60/158,507, filed on Oct. 8, 1999.

(51) Int. Cl.
*A61F 7/00* (2006.01)
*F27D 11/02* (2006.01)
*F27D 19/00* (2006.01)

(52) U.S. Cl. .................. 219/385; 219/394; 219/395; 219/399; 219/428; 604/114

(58) Field of Classification Search .................. None
See application file for complete search history.

(56) References Cited

U.S. PATENT DOCUMENTS

| | | | |
|---|---|---|---|
| 5,609,784 A | 3/1997 | Davenport |
| 5,805,455 A | 9/1998 | Lipps |
| 5,816,797 A | 10/1998 | Shoenfeld |
| 5,862,672 A | 1/1999 | Faries, Jr. et al. |
| 5,961,866 A | 10/1999 | Hansen |

FOREIGN PATENT DOCUMENTS

WO WO 98/45658 10/1998

*Primary Examiner*—William C Doerrler (57) ABSTRACT

A temperature control system includes a cabinet or system housing having a plurality of heating compartments for containing intravenous solution bags or other medical items. Each heating compartment is independently heat controlled via a controller, and includes a heating assembly including a heater, a U-shaped heating plate, a temperature sensor and a cut-out switch for disabling the heater when a threshold temperature is exceeded. The desired or set point temperature for each heating compartment may be independently entered to the controller via an input device. The heating plate has a generally U-shaped configuration with a thermally conductive bottom wall and thermally conductive side walls extending therefrom. The heater is typically affixed to the underside of the bottom wall, wherein, upon heating of the bottom wall, heat is conducted through the side walls to provide an even distribution of heat to medical items placed within the heating compartment. Each heating compartment may further include a collapsible rack structure allowing a user to selectively partition each heating compartment based upon the specific types of medical items to be heated.

EX PARTE REEXAMINATION CERTIFICATE ISSUED UNDER 35 U.S.C. 307

THE PATENT IS HEREBY AMENDED AS INDICATED BELOW.

AS A RESULT OF REEXAMINATION, IT HAS BEEN DETERMINED THAT:

The patentability of claims 1–11, 17–26 and 34–43 is confirmed.

Claims 12–16 and 27–33 are cancelled.

* * * * *